United States Patent [19]

Foulletier et al.

[11] 4,059,626

[45] Nov. 22, 1977

[54] TRIFLUOROETHYLANILINES

[75] Inventors: Louis Foulletier, Oullins; Jacques Pierre Edmond Pechmeze, Paris; Robert Frederic Michel Sureau, Enghien les Bains, all of France

[73] Assignee: Produits Chimiques Ugine Kuhlmann, Paris, France

[21] Appl. No.: 562,063

[22] Filed: Mar. 26, 1975

[30] Foreign Application Priority Data

Mar. 29, 1974 France ................. 74.11263

[51] Int. Cl.² ............. C07C 87/52; C07C 87/56; C07C 91/44; C07C 93/14
[52] U.S. Cl. ................. 260/578; 260/159; 260/207.1; 260/575
[58] Field of Search ............. 260/575, 578, 571

[56] References Cited

U.S. PATENT DOCUMENTS

| | | | |
|---|---|---|---|
| 2,194,925 | 3/1940 | Daudt et al. | 260/575 |
| 2,351,247 | 6/1944 | Weinmayr | 260/578 |
| 2,618,630 | 11/1952 | Dickey | 260/207.3 |
| 2,862,974 | 12/1958 | Sieglitz et al. | 260/578 X |
| 3,453,284 | 7/1969 | Harvey | 260/575 |
| 3,576,876 | 4/1971 | Raper et al. | 260/575 |

*Primary Examiner*—Daniel E. Wyman
*Assistant Examiner*—John J. Doll
*Attorney, Agent, or Firm*—Beveridge, DeGrandi, Kline & Lunsford

[57] ABSTRACT

Compound of the formula:

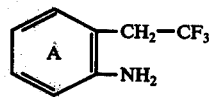

in which the nucleus A is unsubstituted or substituted by one or two nitro, amino, alkyl, alkoxy, chlorine or bromine and the alkyl and alkoxy each contain up to two carbon atoms capable of being used as intermediate products for preparing dyestuffs, pharmaceutical products or phytopharmaceutical products.

2 Claims, No Drawings

TRIFLUOROETHYLANILINES

The present invention concerns trifluoroethylanilines, which are new compounds and are capable of being used as intermediate products for preparing dyestuffs, pharmaceutical products or phytopharmaceutical products.

According to the present invention trifluoroethylanilines are provided having the following general formula:

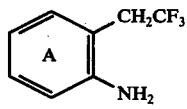

in which the nucleus A is unsubstituted or substituted by one or two nitro, amino, alkyl or alkoxy group or chlorine or bromine atom and the alkyl and alkoxy groups each contain up to two carbon atoms.

It is known that N-(2,2,2-trifluoroethyl) aniline may be prepared by reacting aniline with 1,1,1-trifluoro-2-chloroethane. This reaction is described in U.S. Pat. No. 2,618,630 (column 17, Example Q). It is carried out in a glass apparatus, i.e. in the absence of metallic salts.

However, it has been found that the same reaction, carried out in the presence of a metallic salt, such as an iron, nickel, cobalt or copper salt, produced not only N-(2,2,2-trifluoroethyl) aniline, but also 2-(2,2,2-trifluoroethyl) aniline.

With substituted anilines, such as alkyl- or alkoxyanilines, having at least one free position ortho to the amino group, the corresponding 2-(2,2,2-trifluoroethyl) anilines are also formed.

Anilines of formula I containing nitro, chlorine or bromine substituents in nucleus A may, however, be obtained by nitrating, chlorinating or brominating 2-(2,2,2-trifluoroethyl) N-acyl anilines and subsequently hydrolysing the acyl group.

The invention is illustrated by the following Examples where the parts indicated are parts by weight unless otherwise stated.

EXAMPLE 1

465 parts of aniline and 237 parts of 1-chloro-2,2,2-trifluoroethane are heated for 6 hours at 250°–255° C. in a stainless steel autoclave. After being cooled, the contents of the autoclave are poured into 1000 parts by volume of 2N sulphuric acid. The mixture, which is strongly acidic, is subjected to distillation with steam. The distillate causes an organic layer to be deposited which is dissolved in 500 parts by volume of benzene. This benzene solution is extracted with 4 times 100 parts of N hydrochloric acid. The aqueous phase, rendered alkaline with a solution of caustic soda, is again extracted with benzene. After the benzene has been dried and evaporated, 62 parts of a white solid are obtained which, after recrystallization from hexane, melts at 49° C. The IR and NMR spectra confirm that it is 2-(2,2,2-trifluoroethyl) aniline.

This compound is not formed when the reaction is effected without any metals for example, in a vitrified steel autoclave.

EXAMPLE 2

35 parts of 2-(2,2,2-trifluoroethyl) aniline are dissolved in 100 parts by volume of glacial acetic acid. 40 parts of acetic anhydride are added and the mixture is heated for 2 hours at 110° C. The product which crystallizes massively by cooling is filtered, washed and dried. 34 parts of 2-(2,2,2-trifluoroethyl) acetanilide are obtained, melting point 187° C.

Analysis: Calculated for C% 55.29: H% 4.60: N% 6.45: F% 26.27: $C_{10}H_{10}F_3NO$. Found: C% 55.4: H% 4.64: N% 6.30: F% 25.6.

Gradually, so as not to exceed the temperature of 0° C., 32.6 parts of the acetyl derivative is introduced into 90 parts by volume of $H_2SO_4$ at 66° Be. 6.5 parts of nitric acid (density = 1.52) are added with stirring without exceeding 0° C., the mixture is stirred for 1 hour at this temperature, then for 2 hours whilst allowing the temperature to rise to approximately 20° C. The mixture is poured onto 500 parts of crushed ice. The precipitate is filtered, washed until neutral and dried. 37 parts of 4-nitro-2-(2,2,2-trifluoroethyl) acetanilide are obtained which is recrystallized in acetic acid for analysis - melting point: 238° C.

Calculated for $C_{10}H_9F_3N_2O_3$: C% 45.80: H% 3.43: N% 10.69: Found: C% 45.3: H% 3.07: N% 10.9:

The NMR spectrum confirms that it is the 4-nitro derivative free from any isomer.

53 parts of this nitrated derivative are heated under reflux in a mixture comprising 300 parts by volume of 2N hydrochloric acid and 150 parts by volume of ethanol until completely dissolved. The mixture is cooled and the solution is rendered alkaline by the addition of aqueous caustic soda, then extracted in ether. After evaporation, 43.8 parts of 4-nitro-2-(2,2,2-trifluoroethyl) aniline are obtained which, when recrystallized from toluene, melts at 101° C.

EXAMPLE 3

A mixture comprising 21.7 parts of 2-trifluoroethyl acetanilide, 9 parts of anhydrous sodium acetate, 200 parts of glacial acetic acid and 16 parts of bromine is stirred for 2 hours at ambient temperature, then at 40° C. for 15 minutes, and finally for one hour at 60° C. After cooling, the solution is poured into 500 parts of water. The precipitate is filtered, washed and dried. 23 parts of 2-(2,2,2-trifluoroethyl)-4-bromoacetanilide are obtained, melting point 216° C.

This product is brought back to boiling point for 6 hours in 200 parts of 2N hydrochloric acid and 100 parts of ethanol. After cooling, the mixture is made alkaline by the addition of 70 parts by volume of 30% caustic soda lye. The precipitate is extracted with ether. After the solvent has been evaporated, 19 parts of 2-(2,2,2-trifluoroethyl)-4-bromoaniline are obtained which is recrystallized from hexane for analysis, melting point 100°–101° C.

Analysis: Calculated for 0% 37.79: H% 2.75: N% 5.51: $C_8H_7BrF_3N$. Found: C% 38.5: H% 2.94: N% 5.61.

The compounds of formula I may be used for preparing azo dyestuffs, according to the known process of diazotization-coupling. When, for example, orthotrifluoroethylaniline is diazotised and coupled with 1-phenyl-3-methyl-5-pyrazolone one obtains a dyestuff which, in its disperse state, dyes polyester fibres in a yellow shade. When coupled with 1-dimethylamino-3-acetylaminobenzene, it (i.e. the orthotrifluoroethylaniline) produces a dyestuff which dyes these same fibres in an orange-yellow shade.

We claim:
1. Compound of the formula:

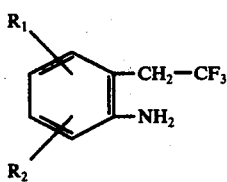
in which $R_1$ is hydrogen, chlorine, bromine or nitro and $R_2$ is hydrogen, chlorine or bromine.
2. The compound 4-nitro-2-(2,2,2-trifluoroethyl)aniline.